US00PP13742P29

(12) United States Plant Patent
Vester

(10) Patent No.: US PP13,742 P2
(45) Date of Patent: Apr. 29, 2003

(54) PHLOX PLANT NAMED 'LITTLE PRINCESS'

(76) Inventor: Mart Vester, 2136 KX, Zwaanshoek (NL)

( * ) Notice: Subject to any disclaimer, the term of this patent is extended or adjusted under 35 U.S.C. 154(b) by 0 days.

(21) Appl. No.: 09/611,214

(22) Filed: Jul. 6, 2000

(51) Int. Cl.[7] ..... A01H 5/00
(52) U.S. Cl. ..... Plt./320
(58) Field of Search ..... Plt./320

(56) References Cited

U.S. PATENT DOCUMENTS

PP11,574 P * 10/2000 Oudshoorn ..... Plt./320

* cited by examiner

*Primary Examiner*—Bruce R. Campell
*Assistant Examiner*—Anne Marie Grünberg
(74) *Attorney, Agent, or Firm*—Klarquist Sparkman LLP

(57) ABSTRACT

A new and distinct variety of Summer Perennial Phlox named 'Little Princess.'

1 Drawing Sheet

LATIN NAME OF THE GENUS AND SPECIES

*Phlox paniculata.*

VARIETY DENOMINATION

'Little Princess'.

BACKGROUND OF THE INVENTION

The present invention comprises a new and distinct variety of Summer Perennial Phlox (*Phlox paniculata*), referred to by the varietal named 'Little Princess.'

This invention has not been observed under all possible environmental conditions. However, the following combination of traits has been repeatedly observed to be firmly fixed in asexually-propagated progeny and is determined to comprise the basic characteristics of this invention. Asexual propagation has been accomplished by division of the original plant, stem cuttings, and root cuttings and has shown that the unique characteristics of this variety are established and transmitted through succeeding asexual propagations. Asexual propagation has been accomplished at a nursery in Zwaanshock, Netherlands and at a greenhouse in Cumming, Ga. Rooting takes about 30 days during the spring season under normal conditions.

The new plant of my invention was obtained by crossing two unreleased nonpatented *Phlox paniculata* plants having the respective designation 90.44.02 and 90.44.06. I was particularly attracted to this plant because of its unique flower color. Plants of this new variety differ from the parental varieties by being more compact than either parental variety and having a different flower color than the female (seed) parent.

BRIEF SUMMARY OF THE INVENTION

The following characteristics, alone or in combination, distinguish 'Little Princess' from other known Summer Perennial Phlox varieties: very short plant habit; resistance to powdery mildew; thick, leathery, dark green leaves; distinctive pink flowers that do not fade in color; long blooming period continuously from midsummer through the fall; excellent garden performance and good weather tolerance; excellent container plant because of its short habit.

BRIEF DESCRIPTION OF THE DRAWING

The accompanying illustration is a view of one entire 'Little Princess' plant of my invention. This illustration is a reproduction of a photograph of my new plant taken in the Netherlands.

DETAILED BOTANICAL DESCRIPTION

The following is a detailed description of a one-year old 'Little Princess' plant. Phenotypic characteristics may change according to growth or environmental conditions, including lighting under which colors are observed. All plants of the new variety, insofar as I have been able to observe them, are identical in all the characteristics described below. Color references are provided according to The R.H.S. Colour Chart published by The Royal Horticultural Society of London, England, except where the context indicates a term having its ordinary dictionary meaning.

Species: *Phlox paniculata.*
Form: Upright, conical, clump forming perennial.
Size: Height of plant from soil line is about 50 cm, spreading about 21 cm in diameter.
Growth rate: Approximately 29 weeks are required in Zwaanshock, Netherlands to produce a fully-grown flowering plant from a cutting when grown in a 1.5 litre container.
Stems/branches: Sufficiently strong to support flowers without staking.
Branching characteristics:
- *Branching habit.*—Basally branching with heavy upper lateral branches.
- *Internode length.*—About 1.5 cm.
- *Diameter.*—About 0.4 cm.
- *Texture.*—Glabrous.
- *Color.*—Green (138B).

Leaves:
- *Typical size.*—About 5 to 13 cm long.
- *Shape.*—Oblanceolate.
- *Texture.*—Slightly ribbed, leathery, and thick.
- *Arrangement.*—Opposite and in pairs; generally symmetrical with long persisting quality per lateral branch.

*Aspect.*—Horizontal.
*Margin.*—Entire.

Color:
*Young foliage — upper surface.*—Green (137A).
*Young foliage — lower surface.*—Green (138A).
*Mature foliage — upper surface.*—Green (137A).
*Mature foliage — lower surface.*—Green (138A).

Venation: Venation pattern is pinnate; venation color on both upper and lower surfaces of leaves is green (143A).

Petiole: About 0.2 cm long and about 0.2 cm in diameter; yellow-green (151A) in color.

Reproductive organs:
*Stamens.*—Five in number, fused with the petals in the flower tube.
*Anther.*—Shape is dorsifixed, size is about 0.5 cm, and color is yellow (2D).
*Pollen.*—Produced in moderate amounts and yellow (2D) in color.
*Pistils.*—Length is about 1.9 cm.
*Stigma.*—Color is yellow-green (154D).
*Style.*—Length is about 1.5 cm and color is yellow-green (154D).
*Ovary.*—Green (141A to 141B) in color.

Flower:
*Arrangement.*—Flowers are borne in large, dense pyramidal panicles measuring an average of 6 inches across with 10 to 18 flowers per panicle facing upright or outward; individual flowers are tubular with a diameter of about 3.9 cm and depth (tube length) of about 2.25 cm.
*Persistence.*—Very persistent.
*Petals.*—Number: Five petals per individual flower; fused. Size: Lobe length (beyond tube) is about 2 cm and petal width is about 2.25 cm. Surface: Flat, though some petals may be slightly curved upwards, and smooth in texture. Color: Outer tips of petals are red-purple (RHS 63A) fading to medium pink in the middle, with a white eye surrounded by a red-purple (RHS 63C) ring.
*Flower bud.*—Tubular in shape with a diameter of about 0.7 cm and a length of about 2.5 cm; purple (75C) in color.
*Scent.*—Faint to moderately sweet fragrance.
*Bloom.*—Freely flowering; initial bloom in Georgia begins in mid- to late-May with rebloom occurring until frost; excellent rebloom; individual flowers last about 5 to 6 days, and the entire plant blooms.

Seed:
*Type.*—Capsule.
*Size.*—About 0.3 cm in length and 0.15 cm in diameter.
*Color.*—Dark brown.
*Pest, climate, and disease resistance.*—Exhibits good tolerance to rain, wind, and low temperatures, with excellent garden performance; resistant to powdery mildew, exhibiting excellent foliage quality throughout the growing season.

I claim:

1. A new and distinct variety of Summer Perennial Phlox named 'Little Princess,' substantially as herein shown and described.

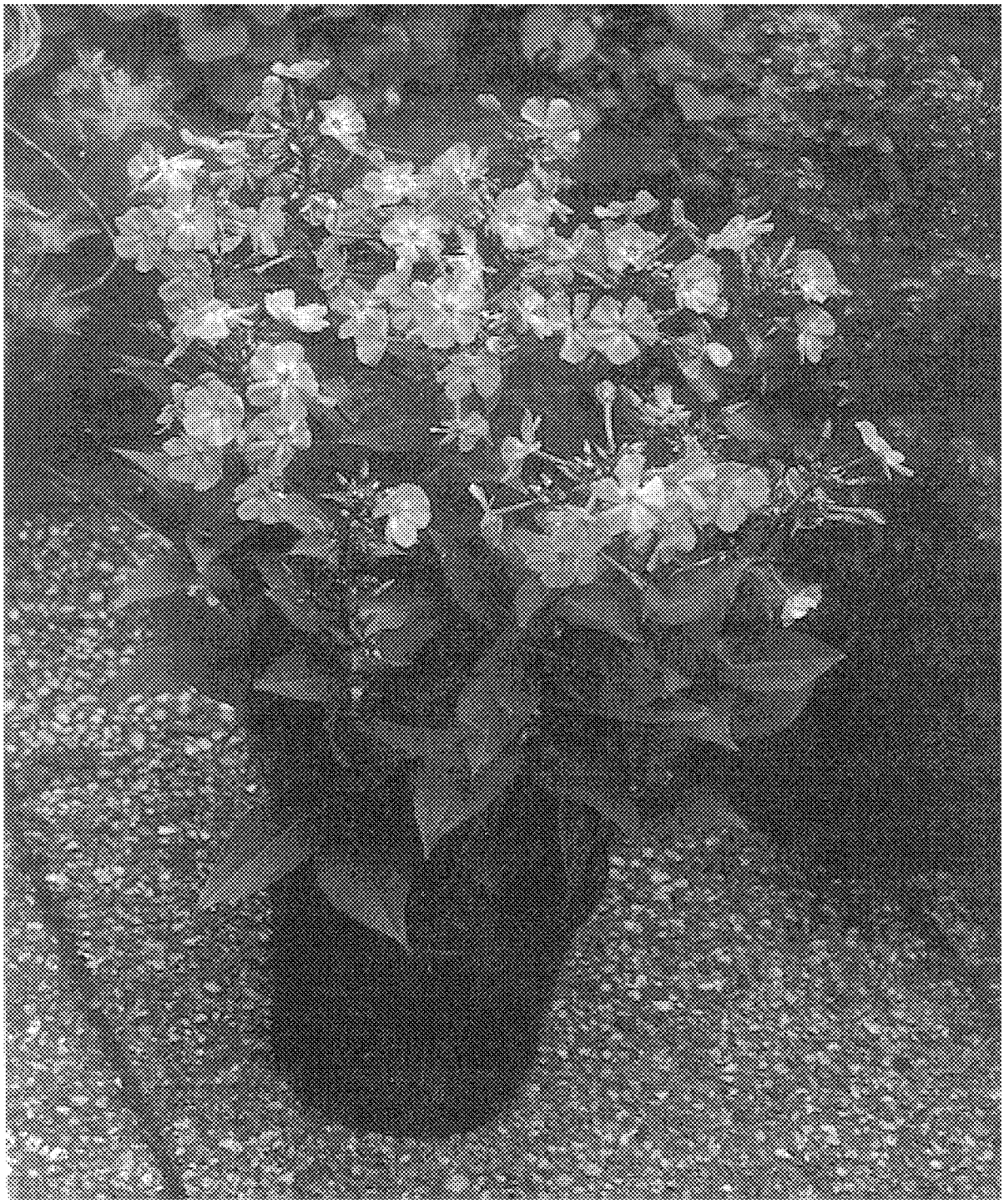

* * * * *